United States Patent [19]

Caldwell et al.

[11] Patent Number: 4,497,768

[45] Date of Patent: Feb. 5, 1985

[54] APPARATUS AND METHOD FOR QUANTITATIVELY EVALUATING TOTAL FISSILE AND TOTAL FERTILE NUCLIDE CONTENT IN SAMPLES

[75] Inventors: John T. Caldwell, Los Alamos; Walter E. Kunz, Santa Fe, both of N. Mex.; Michael R. Cates, Oak Ridge, Tenn.; Larry A. Franks, Santa Barbara, Calif.

[73] Assignee: The United States of America as represented by the United States Department of Energy, Washington, D.C.

[21] Appl. No.: 395,893

[22] Filed: Jul. 7, 1982

[51] Int. Cl.³ .............................................. G21C 17/00
[52] U.S. Cl. .................................... 376/153; 376/157; 376/257
[58] Field of Search ............... 376/257, 157, 153, 156

[56] References Cited

U.S. PATENT DOCUMENTS 2,902,613  9/1959  Baldwin et al. ..................... 376/156
3,496,357  2/1970  Weinzierl et al. ................... 376/257
3,636,353  1/1972  Untermyer et al. ................. 376/257

FOREIGN PATENT DOCUMENTS 666943  7/1963  Canada ............................... 376/257

OTHER PUBLICATIONS

Nucl. Inst. & Meth., 193, 571 (1982) Franks et al.

Primary Examiner—Sal Cangialosi
Attorney, Agent, or Firm—Samuel M. Freund; Paul D. Gaetjens

[57] ABSTRACT

Simultaneous photon and neutron interrogation of samples for the quantitative determination of total fissile nuclide and total fertile nuclide material present is made possible by the use of an electron accelerator. Prompt and delayed neutrons produced from resulting induced fissions are counted using a single detection system and allow the resolution of the contributions from each interrogating flux leading in turn to the quantitative determination sought. Detection limits for $^{239}$Pu are estimated to be about 3 mg using prompt fission neutrons and about 6 mg using delayed neutrons.

19 Claims, 4 Drawing Figures

APPARATUS AND METHOD FOR QUANTITATIVELY EVALUATING TOTAL FISSILE AND TOTAL FERTILE NUCLIDE CONTENT IN SAMPLES

This invention is the result of a contract with the Department of Energy (Contract No. W-7405-ENG-36).

BACKGROUND OF THE INVENTION

The present invention relates generally to the quantitative evaluation of total fissile and total fertile nuclide content in samples, and more particularly to simultaneous photon and neutron interrogation of a sample coupled with the measurement of resulting prompt and delayed neutron emission as the basis for analysis of the totality of the fissile material present in the form of $^{233}$U, $^{235}$U or $^{239}$Pu, and the totality of fertile material present in the form of $^{232}$Th and $^{238}$U in the sample under investigation.

Current U.S. Department of Energy guidelines for the management of transuranic waste have created a need for instrumentation to monitor such wastes at the 10 nCi/g level of fissile nuclides in the presence of fertile material. Solely passive systems which rely on the detection of gamma rays or neutrons from the decay or spontaneous fission of transuranic wastes are generally not suitable because of (1) the attenuation of high density matrix material with the attendant loss of sensitivity, and (2) interference from gamma and alpha emitting contaminants in the matrices. Active interrogation methods, wherein the waste is probed by an externally generated neutron or photon pulse, which cause fission in many of the nuclides present, or a combination of active and passive methods, overcome many of the problems associated with the passive methods alone. Two currently used active methods are: (1) photofission where a high energy photon beam induces fission in the waste sample and fission and delayed neutrons thereby produced are detected, and (2) thermal neutron fission where fast neutrons from a pulse source, after moderation, induce fissions in those nuclides present in the sample which are fissile. Active assay systems based on these methods have been used but neither approach itself is entirely adequate. Photofission offers good sensitivity for a large number of transuranic waste samples, but because of similarity of photofission cross-sections, identification of specific nuclides or classes of nuclides is difficult. For example, the important fissile and fertile groups cannot readily be distinguished. Thermal neutrons, on the other hand, offer very high sensitivity for fissile elements but essentially none for fertile elements. A combination of the two methods would be most desirable but technical complexities such as the need for two pulsed sources, together with longer assay times, have made such an analytical system impracticable.

A combination of neutron and photon interrogation offers several distinct advantages over either applied alone, including a direct and unequivocable separation of fissile and fertile nuclides within the sample under investigation. The method and apparatus of the instant invention demonstrates that dual interrogation can be achieved using an electron linear accelerator (LINAC) as a pulsed source for both photons and neutrons. Moreover, both interrogations are initiated during each pulse of the LINAC, and the resulting prompt and delayed neutrons can be monitored with the same detection system.

It is known in the art that high energy gamma radiation is produced as a result of bremsstrahlung in a heavy-metal target placed in the path of a high energy electron beam. The production of neutrons through the use of electron beams is also known, and occurs when the high energy gamma photons subsequently pass through additional layers of a target causing neutrons to be emitted in ($\gamma$,n) processes. "Efficient Neutron Production Using Low-Energy Electron Beams," by C. D. Bowman, Nucl. Sci. Eng., 75, 12 (1980). However, the combination of neutrons and gamma radiation produced from a single source and used for analysis of transuranic waste samples for total fissile and total fertile nuclides present has not been reported.

Most of the photons will pass into the volume of the waste sample where some will cause photofission. Prompt neutrons emitted from the photofission of either fissile or fertile nuclides will not be distinguishable from photoneutrons that are formed in the materials of the chamber containing the sample under investigation and/or the matrix materials which contain these fissile and fertile nuclides. However, delayed neutrons from photofission will be emitted on a continual basis during the whole period between LINAC pulses. Photoneutrons and prompt photofission neutrons will thermalize in a few tens of microseconds and will persist as thermals for hundreds of microseconds, during which time they will generate thermal neutron fissions among the fissile transuranic nuclides that may be present. Therefore, fission neutrons from thermal fission are separated in time from the photoneutrons, and can serve, along with delayed neutrons, as a quantitative signature. Essentially then, after an initial burst of photoneutrons and neutrons from photofission, the bulk of the fast prompt neutrons derive from thermal fission of fissile materials. Subsequent to the emission of these prompt neutrons are the emission of delayed neutrons which derive from both photofission of fertile and fissile material as well as delayed neutrons from thermal neutron fission of fissile nuclides. If the latter contribution to the total delayed neutron flux is made small, the delayed neutron emission is representative of the photofission events only. To achieve this result, some iteration of the interrogation neutron flux may be necessary when analyzing samples of completely unknown fissile content. This flux can be varied by choosing different target materials for the ($\gamma$,n) source.

Thus, in the instant invention, the events detected following a single LINAC pulse are separable into neutron fission (prompt fission neutrons) and photofission (delayed neutrons) events. This data can then be analyzed to yield the individual quantities of fertile and fissile isotopes present.

SUMMARY OF THE INVENTION

An object of the apparatus and method of the instant invention is to quantitatively evaluate total fissile and total fertile nuclide content in samples.

Another object of our invention is to screen transuranic wastes for storage arrangements at the 10 nCi/g level.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

To achieve the foregoing and other objects in accordance with the purpose of the present invention, as embodied and broadly described herein, the method of this invention may comprise generating repetitively pulsed gamma radiation and neutrons, using these radiations to interrogate the sample of interest, and detecting the emitted prompts and delayed fast neutron flux. High energy repetitively pulsed gamma radiation is generated and directed onto a partially transparent target from which photoneutrons are generated while allowing a substantial portion of the gamma radiation to pass through. The transmitted gamma radiation and generated photoneutrons are then allowed to simultaneously impinge on a chamber which surrounds and contains the sample under investigation. The photoneutrons are then thermalized by collisions within the walls of the chamber resulting in an enhanced probability that any fissile isotopes present within the sample will undergo a fission reaction. The high energy gamma radiation causes photofission in both the fertile and fissile materials, while the thermalized neutrons produce fission in only the fissile material present. From the actual fission processes, and from the fragments produced therefrom, both prompt and delayed fast neutrons are emitted. These emitted neutrons, along with the thermalized photoneutron flux, are measured in between the gamma radiation pulses. A plurality of such measurements are accumulated until a statistically significant signal is obtained, and the results, normalized by the accumulated thermalized neutron flux and gamma radiation photon flux, are related to the total fissile and the total fertile nuclide concentration contained in the sample to be quantitatively assayed, using known gamma and neutron cross-sections for these nuclides. Preferably, the pulsed gamma radiation has a photon energy in excess of about 10 MeV in order to produce significant numbers of photoneutrons. Preferably, also, the photoneutrons are thermalized within about 0.5 ms after the termination of a particular gamma radiation pulse. Since the fissile nuclides undergo both photofission and thermal neutron fission, the delayed neutron emission is composed of contributions from both the fertile nuclides and the fissile nuclides. Therefore, the gamma radiation generated neutron flux is adjusted such that the emitted delayed neutron flux is comprised principally of neutrons from only the photofission reactions, while allowing sufficient prompt fast neutron emission from the thermal neutron fission process in the fissile nuclides to enable statistically significant neutron measurements to be obtained in a practical accumulation time period. This is possible because of the high sensitivity of the method for prompt fast neutron emission, derived from the temporal and energy selectivity of the $^3$He-proportional counting system utilized. Preferably, prompt fast neutron measurements are made between about 0.5 and and 2.5 ms after the termination of a particular gamma radiation pulse, and this measurement determines the number of thermal-neutron-induced fissions. The delayed fast neutron measurements are performed between about 5.5 ms after the termination of a particular gamma radiation pulse and the commencement of the following gamma radiation pulse. Adjustment of the thermal-neutron interrogating flux, if necessary, is performed by allowing larger or smaller amounts of photoneutron emitters to be placed in the gamma radiation beam pathway. It is also preferred that the gamma radiation is derived from an electron accelerator, the high energy electrons produced therefrom, being caused to impinge upon a metal target thereby producing the desired radiation by a bremsstrahlung process. It is finally preferred that the photoneutron emitting target include beryllium.

In a further aspect of the present invention, in accordance with its objects and purposes, the apparatus hereof may also comprise means for simultaneously generating repetitively pulsed gamma radiation and photoneutrons produced therefrom, a chamber which surrounds and contains the sample under investigation and into which the neutrons and gamma radiation are directed, means for thermalizing these photoneutrons to increase their fission reaction effectiveness for fissile nuclides present in the sample, means for measuring the thermalized photoneutron flux in the vicinity of the sample and for measuring prompt and delayed fast neutron emission from the sample as a result of photofission of fertile and fissile nuclides interacting with the gamma radiation, and from thermal neutron fission of fissile nuclides capturing thermalized photoneutrons during a time interval after the termination of the gamma radiation pulse, and the means for accumulating a plurality of such neutron measurements until a statistically significant signal is obtained and means for recording these accumulated measurements. Preferably, the thermalization of the photoneutrons occurs within the walls of the chamber. It is also preferred that the thermalized photoneutron flux is measured using at least one bare low partial pressure $^3$He-proportional counter located inside the chamber in the vicinity of the sample, and the prompt and delayed fast neutron emission measurements are made using at least one high pressure $^3$He-proportional counter surrounded by polyethylene which is further surrounded by cadmium foil and located within the chamber in the vicinity of the sample. Such shielded detectors block the large thermalized photoneutron background while allowing very sensitive prompt fission neutron detection. Preferably also, the gamma radiation is produced by means of an electron accelerator capable of providing greater than about 1 ma of electron beam current in short duration pulses at a repetition rate between 1 and 60 Hz and at energies in excess of about 10 MeV, said electrons impinging upon a heavy metal target producing high-energy gamma radiation by means of a bremsstrahlung process. Preferably, the pulsed gamma radiation is filtered to remove photons of low energy to reduce the gamma radiation background, and to remove background neutrons from the bremsstrahlung target using a polyethylene slab placed in between the bremsstrahlung target and the chamber. The polyethylene slab often provides sufficient photoneutrons for thermal fission interrogation without the need for the presence of beryllium which is sometimes inserted in the polyethylene slab in small quantities in the path of the gamma radiation. It is also preferred that the chamber wall be constructed of a thick polyethylene and graphite inner wall surrounded by a layer of cadmium foil which is further surrounded by a thick outer wall of borated polyethylene in order to reduce the effect of stray neutrons generated by the electron accelerator away from the direction of the electron beam, since it is desired that the interrogation neutrons originate in the chamber, and to thermalize the photoneutrons incident on this chamber.

Finally, it is preferred that the number of neutrons generated from the pulsed gamma radiation is controlled by selection of a suitable target material which for low neutron flux requirements is simply the chamber wall, and for high neutron flux requirements may include a beryllium sheet placed in between the gamma radiation filter and the chamber.

In summary, the apparatus and method of the instant invention allows the distinguishing of fissile and fertile nuclides in a sample under investigation, which is not available from separate interrogation by either neutrons or gamma radiation alone. For example, thermal neutron interrogation offers very high sensitivity for fissile elements but essentially none for fertile nuclides. It is important that the fertile elements be measured since a particular assay for fissile nuclides made alone cannot identify the material as being of low enrichment (small fissile-to-fertile ratio) or high enrichment (large fissile-to-fertile ratio). For proper disposal and handling a fissile-to-fertile ratio is required. The simultaneous production of pulsed gamma radiation and thermal neutrons from a single source provides great simplification for the experimental procedures necessary to do the assay of samples, and also greatly reduces the time involved in performing such assays.

BRIEF DESCRIPTION OF THE DRAWINGS

The accompanying drawings, which are incorporated in and form a part of the specification, illustrate an embodiment of the present invention and, together with the description, serve to explain the principles of the invention. In the drawings.

DETAILED DESCRIPTION OF THE INVENTION

Reference will now be made to the present preferred embodiment of the invention, an example of which is illustrated in the accompanying drawings.

Figure 1:
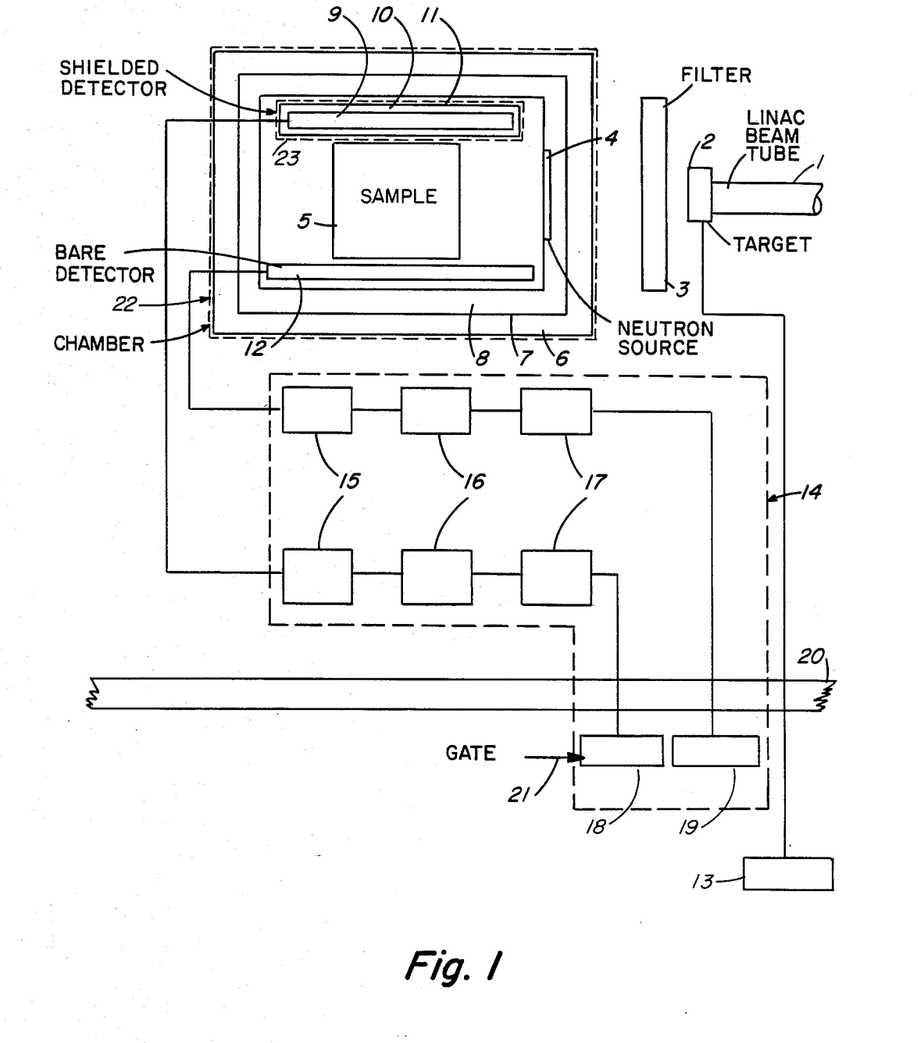
FIG. 1 is a schematic representation of the apparatus of the instant invention.

FIG. 1 is a schematic representation of the apparatus of the instant invention. Gamma radiation photons are produced in a bremsstrahlung target 2 affixed to the LINAC beam tube terminus. The photons then pass through a polyethylene slab 3 which hardens the photon spectrum by preferentially filtering out photons of energy less than about 2 MeV. Some portion of the higher energy photons which pass through the filter (those above various reaction threshold energies) will produce photoneutrons in the neutron source 4. As will be discussed below, it is often unnecessary to provide a separate target to produce neutrons as photoneutrons in sufficient quantities may be produced in the walls of the chamber. Most of the photons will pass into the volume of the chamber 22 which contains the waste sample 5 where some will cause photofissions. Prompt photofission neutrons, emitted from the interaction of gamma ray photons with matter in their path, will not be distinguishable from photoneutrons that are formed in the materials comprising the sample chamber. They therefore contribute to the overall flux of thermal neutrons. However, delayed neutrons from photofission processes are emitted continuously during the entire period between LINAC pulses, and therefore their measurement provides important information as to the contents of the sample. Photoneutrons and prompt photofission neutrons will thermalize in a few tens of microseconds and will persist as thermal neutrons for hundreds of microseconds, during which time they will generate thermal-neutron-fissions among fissile nuclides present in the sample.

Prompt fission neutrons emitted from thermal fission are thus separable from the photoneutrons by use of time and energy discrimination and can serve along with the delayed neutrons from the photofission as an important quantitative analytical measurement. Means are provided for detection of both the thermalized neutron flux and the fast prompt and delayed neutron flux. Prompt and delayed fast neutron emission can be measured during the thermal die-away time using a fast neutron sensitive moderated $^3$He-proportional counter 23, which is shielded from the thermal neutron flux by cadmium 11, in the preferred embodiment of the instant invention. This detector also provides discrimination against any gamma radiation emissions during the counting period since such gammas generate much lower pulse heights in the detector and can be removed electronically from the signal of interest.

Means are provided for generating an intense electron beam with maximum electron energies in excess of 10 MeV, since the photons to be generated therefrom must have at least this energy in order to produce significant photofissions and photoneutrons in their interaction with the materials upon which they impinge. Preferably, electron energies of about 12 MeV are provided with a pulse width of about 4 μs. It is also preferred that the repetition rate lie between 1 and 60 Hz and the peak current between approximately 1 and 200 ma. Bremsstrahlung radiation can be generated in heavy metal targets 2 attached to the terminus of the electron accelerator beam tube 1. In a preferred embodiment of the apparatus of the instant invention an EG&G LINAC was employed. A 10 cm thick polyethylene slab 3 was placed in front of the target to harden the photon spectrum as mentioned above. The samples under investigation 5 and the neutron detectors 12, 23, were contained within a polyethylene enclosure 8 with internal dimensions 35×38×61 cm and 10 cm wall thickness. The outside of the enclosure was covered with 0.6 mm cadmium sheet 7 and a 10 cm thick layer of borated polyethylene 6 to reduce the effects of neutrons generated elsewhere in the concrete irradiation zone 20. In a preferred embodiment of the apparatus of the instant invention, a single 5 cm diameter × 34 cm long proportional counter 9 filled to three atmospheres of $^3$He served as the primary fast neutron detector. The tube was encased in 1.25 cm of polyethylene 10 which was in turn wrapped with 1.7 mm of cadmium 11. This thickness of cadmium provides an attenuation factor for thermal neutrons of approximately $10^8$. A 2.5 cm diameter × 51 cm long bare tube 12 containing 1% $^3$He (99% $^4$He) at low pressure was used as a neutron flux monitor. The LINAC beam current was monitored at the target 2 to provide normalization for the photofission yields.

The proportional counter outputs were fed to singly-differentiating preamplifiers 15, which were in turn fed to linear amplifiers 16 and then to single-channel analyzers 17. The detected pulses were then directed to scalers 18, 19 outside of the irradiation cell. The scalers were gated on 21 after each LINAC burst by a pulse from the LINAC injector. Signals from both the primary detector and the flux monitor were summed during the irradiation, as was the LINAC beam current.

Figure 2:
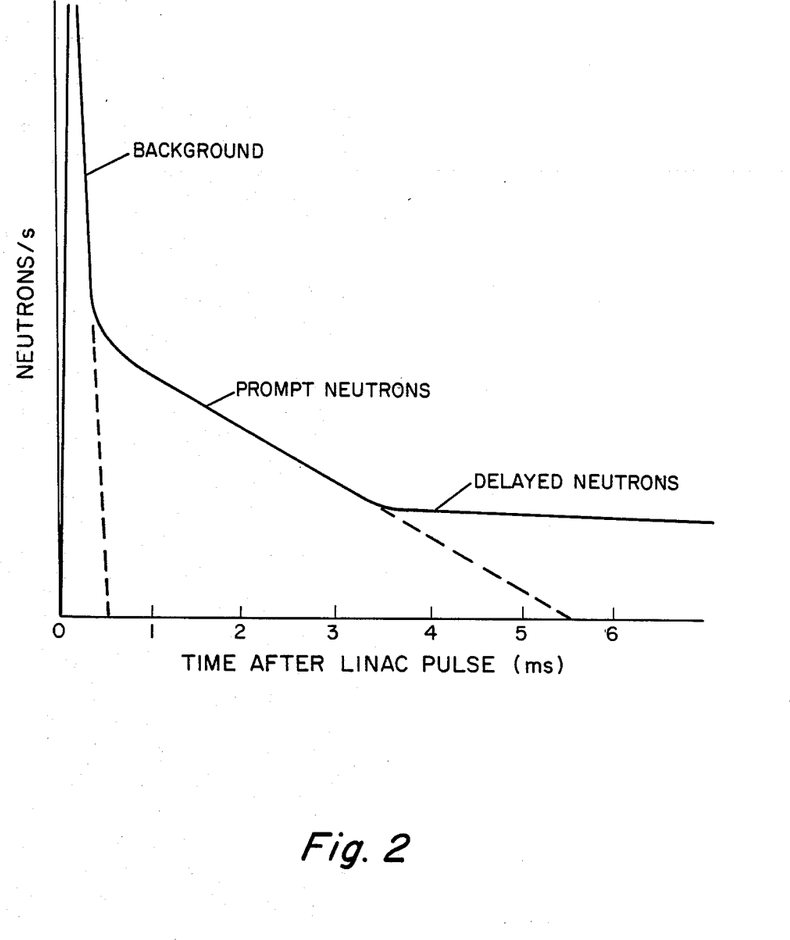
FIG. 2 depicts the time sequence of emitted neutrons after an interrogation pulse of gamma radiation and photoneutrons.

FIG. 2 depicts the time sequence of emitted neutrons after an interrogation pulse of gamma radiation and photoneutrons. The first few hundred microseconds following the LINAC pulse are dominated by photoneutrons and prompt neutrons from photofission. Detection of these neutrons is complicated by residual effects of the intense gamma flux and electromagnetic noise on the counting system. The remainder of the first half millisecond is typically a period during which the initially fast neutrons are thermalized. The next two milliseconds (0.5–2.5 ms) is the period in which fast prompt neutrons from thermal-neutron-induced fissions are measured with the cadmium-wrapped detector 23. A second period, after the thermal interrogating flux has subsided, includes most of the remaining time before the next LINAC pulse (5.5–25.5 ms). During this period there is an approximately constant level of fast-neutron signal arising from delayed neutron emission. The first counting segment then, is generally dominated by counts from fissile nuclides present, and the second segment by counts from both fertile and fissile nuclides which have undergone photofission. It is arranged such that this later signal is comprised principally of neutrons from photofission by reducing the number of thermally-induced-fissions occuring while still maintaining a sufficiently strong prompt neutron signal to enable good signal statistics in a practical accumulating time period. This is achieved by controlling the number of thermal neutrons in the chamber.

Figure 3:
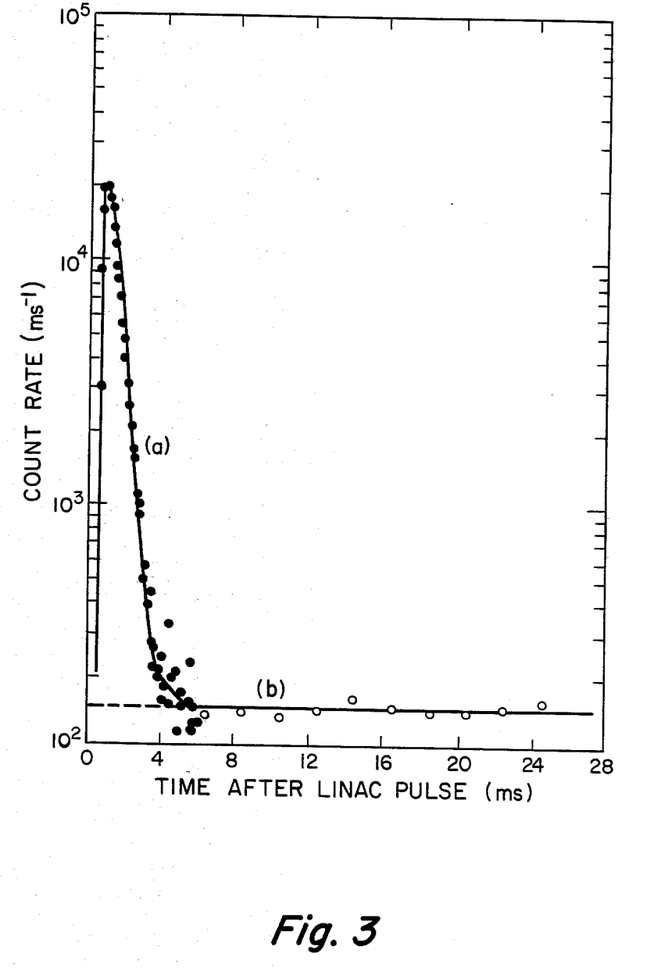
FIG. 3 displays the time history of the observed neutron count rate arising from the simultaneous photon and neutron interrogation of 1 g of $^{233}$U.

FIG. 3, curves a and b, display the time history of the observed neutron count rate arising from the simultaneous photon and neutron interrogation of 1 g of $^{233}$U which is a fissile nuclide. Curve a shows the $^{233}$U thermal-neutron-fission reaction neutrons, while Curve b shows the delayed neutron emission, 97% of which is from $^{233}$U photofission reactions. A LINAC beam energy of 12 MeV, a pulse width of 4 μs, and a repetition rate of 30 Hz were used to obtain the data in FIG. 3. The peak beam current was about 200 ma and about 20,000 interrogating pulses were accumulated. Samples 5 were positioned at the center of the chamber 22 along the beam line at a point approximately 1 m from the bremsstrahlung target 2. Background count rates were obtained by irradiating with the samples removed. Net prompt neutron counts were normalized to the neutron flux monitor counts, and the delayed neutrons to the electron beam current monitor counts.

Figure 4:
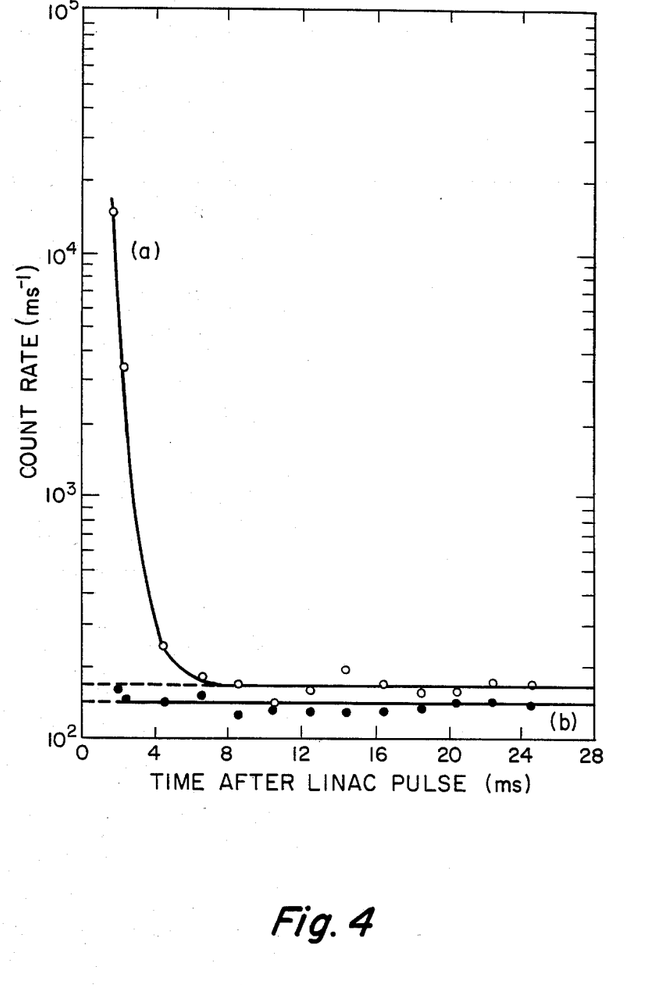
FIG. 4 displays the time history of the neutron count rate arising from the simultaneous photon and neutron interrogation of 1 g of $^{239}$Pu.

FIG. 4, Curves a and b, display the time history of the neutron count rate arising from the simultaneous photon and neutron interrogation of 1 g of $^{239}$Pu. Here the contribution of each of the interrogating fluxes to the prompt and delayed neutron counts was investigated by comparing the detector response to a plutonium sample covered with an about 1.8 mm thick cadmium cover (Curve b), and to one without such a cover (Curve a). It is seen that the delayed neutrons are only weakly affected by the cadmium whereas the thermally-induced-fission, prompt neutrons are essentially absent with the cadmium present. This means that the photofission process (where the cadmium cladding should have a negligible effect) is the primary source of the delayed neutrons. In other words, by wrapping the plutonium sample, in the form of $PuO_2$, thermal fission neutrons are prevented from reaching the fissile nuclides thereby preventing any thermal-neutron-fission neutron emision from contributing to the delayed neutron flux. Gamma radiation, on the other hand, easily passes through such a thin sheet of cadmium, and since they are of substantially greater energy than that required to cause photofission in plutonium, a substantial number of photofission neutrons are produced. The LINAC conditions were identical to those used in FIG. 3.

To illustrate the method of this invention, the following examples are presented.

The results of irradiating $^{239}PuO_2$ with masses of 1, 0.2, and 0.05 g appear in lines 1–3 of Table 1. The background during both the thermal-fission prompt neutron region (0.5–2.5 ms) and the delayed neutron region (5.5–25.5 ms) was about 1% of the signal for the 1 g sample (line 8). This implies a similar sensitivity for the two counting periods. The net delayed neutron counts are approximately proportional to the quantities of the three masses investigated. However, the net prompt neutron counts were found to be reduced because of the self-masking effect most notably in samples of plutonium. That is, for compact samples (each sample was oxide powder in a doubly-encased, stainless steel cylinder about 3 cm long, 1 cm in diameter, with a total wall thickness of about 1.8 mm), the larger masses absorbed a sufficient number of thermal neutrons in their outer layers to lower the apparent effective mass of the entire sample. This is not a problem for delayed neutrons arising from photofission events. A useful feature of the simultaneous interrogation method of the instant invention is that the presence of photofission neutrons can, in certain cases, provide an internal measure of the masking effect. Self-masking is not a serious problem for waste samples since the fissile material density is generally low.

TABLE 1

| Line number | Sample | Prompt neutron region (0.5–2.5 ms) | | Delayed neutron region (5.5–25.5 ms) | | Delayed Prompt | Linac pulses |
| --- | --- | --- | --- | --- | --- | --- | --- |
| | | Gross counts | Net normalized counts | Gross counts | Net normalized counts | | |
| 1 | $^{239}$Pu (1 g) | 11081 | 1.418 | 1850 | 0.114 | 0.080 | 20,006 |
| 2 | $^{239}$Pu (0.2 g) | 2140 | 0.554 | 190 | 0.020 | 0.036 | 10,008 |
| 3 | $^{239}$Pu (0.05 g) | 1904 | 0.188 | 153 | 0.007 | 0.037 | 20,001 |
| 4 | $^{233}$U (1 g) | 19570 | 2.218 | 2987 | 0.150 | 0.068 | 20,010 |
| 5 | $^{235}$U (0.19 g) | 4999 | 0.501 | 946 | 0.047 | 0.094 | 20,004 |
| 6 | $^{238}$U (1.5 g) | 412 | 0.036 | 3939 | 0.196 | 5.44 | 20,003 |
| 7 | $^{238}$U (1.5 g) plus $^{239}$Pu (1 g) | 11855 | 1.40 | 6739 | 0.356 | 0.254 | 20,007 |

TABLE 1-continued

| | | Prompt neutron region (0.5–2.5 ms) | | Delayed neutron region (5.5–25.5 ms) | | | |
|---|---|---|---|---|---|---|---|
| Line number | Sample | Gross counts | Net normalized counts | Gross counts | Net normalized counts | Delayed Prompt | Linac pulses |
| 8 | background | 100 | 0.012 | 13 | 0.0006 | — | 20,001 |

Yields from 1 g of $^{233}$U, 0.20 g of $^{235}$U and 1.5 g of $^{238}$U are given in Table 1, lines 4, 5, 6, respectively. The potential of the apparatus and method of the instant invention for distinguishing between fertile and fissile components of transuranic waste is illustrated by the results for $^{238}$U (line 6). That is, the lack of a significant thermal fission cross-section in $^{238}$U relative to the fissile nuclides is clearly shown by the high delayed-to-prompt-neutron ratio for $^{238}$U. Although the depleted uranium used did contain a small amount of $^{235}$U which contributed a small thermal fission yield, the presence of a more significant fissile nuclide concentration is easily handled by reducing the number of thermal neutrons available for capture by such fissile nuclides such that the fissile nuclide contribution to the delayed neutron flux is minimized while sufficient prompt neutrons exist for their determination. Even when this is not done, as for the results of a mixture of $^{238}$U and $^{239}$Pu, illustrated in line 7 of Table 1, it is very easy to tell that there are both fissile and fertile nuclides present. The net normalized prompt neutron flux is clearly the result of about 1 g of $^{239}$Pu as can be derived from line 1 of the table, while the net normalized delayed neutron flux can be seen to be the result of about 1 g of $^{239}$Pu and about 1.5 g of $^{238}$U (lines 1 and 6). Moreover, the delayed-to-prompt ratio has a value of 0.25, so that even where a substantial fissile nuclide concentration exists in the sample, it is easily observed that there must be a substantial fertile nuclide concentration by simply observing this ratio.

The sensitivity of a preferred embodiment of our invention was estimated using a $3\sigma$ criterion wherein the minimum detectable signal is taken to be three times the square root of the background. Background counts were typically 100 and 13 in the prompt- and delayed-neutron measurement intervals, respectively, as is seen in line 8 of Table 1. In the case of 1 g $^{239}$Pu, the net delayed neutrons are measured to be about 170 times the $3\sigma$ value of 11, which gives a lower limit of detectability of about 6 mg. A similar treatment of the prompt-neutron yield of 1 g $^{239}$Pu gives a lower limit of about 3 mg. No corrections were made for matrix effects, and the detection system had only one $^3$He detection tube. Further, counting times were limited to about 11 min. By adding detectors to the system, increasing the counting time, or increasing the beam current, which in turn would increase the number of interrogation photons, the system sensitivity can be markedly improved. The quoted sensitivities can be converted to units which the United States Department of Energy uses, which translates to the fact that our invention can be used to assay plutonium contents of less than 10 nCi/g in 208 l (55 gal.) barrels.

In summary, the apparatus and method of the instant invention can be used to determine the total fissile nuclide concentration and the total fertile nuclide concentration in a sample of transuranic waste by the use of simultaneous neutron and gamma radiation interrogation of the sample. An electron linear accelerator through the bremsstrahlung effect produces sufficient photons and photoneutrons in each electron pulse to perform sample analyses with high sensitivity. In so doing, the advantages of simultaneous photon interrogation and neutron interrogation can be realized along with the simplicity of a single source- and sample-handling system. Moreover, the prompt and delayed neutrons produced in the induced fissions can be counted using the same detection system and the same geometry, and since they are clearly separable temporally, the thermal neutron and photofission contributions to this emitted fission neutron flux are easily and quantitatively discernible.

The foregoing description of the preferred embodiment of the invention has been presented for purposes of illustration and description. It is not intended to be exhaustive or to limit the invention to the precise form disclosed, and obviously many modifications and variations are possible in light of the above teaching. For example, any electron accelerator providing greater than about 1 ma of beam current at electron energies in excess of about 10 MeV, and capable of operation at pulse rates between about 1 and 50 Hz can be used to provide an appropriate source of photons and photoneutrons for the sample interrogation.

The embodiment was chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A method for quantitatively evaluating total fissile and total fertile nuclide content in samples, which comprises the steps of:
  a. generating repetitively pulsed gamma radiation;
  b. directing said gamma radiation onto a partially transparent target which generates photoneutrons while allowing a substantial portion of said gamma radiation to pass through;
  c. thermalizing said photoneutrons such that their reaction probability with fissile isotopes is substantially enhanced;
  d. causing said gamma radiation and said thermalized photoneutrons to impinge upon a sample;
  e. measuring the flux of said thermalized photoneutrons in the vicinity of the sample during time intervals in between the termination of a particular gamma radiation pulse and the commencement of the following one;
  f. measuring the intensity of said gamma radiation in the vicinity of the sample;
  g. measuring prompt and delayed fast neutron emission from the sample resulting from photofission of fertile and fissile nuclides interacting with said impinging gamma radiation, and from fission of fissile nuclides capturing said thermalized photoneutrons during said time intervals;
h. accumulating a plurality of said prompt and delayed fast neutron emission measurements, and a plurality of said thermalized neutron flux measurements until statistically significant measurements are obtained; and
i. relating said accumulated emitted prompt and delayed fast neutron measurements normalized by said accumulated thermalized neutron flux measurements and said intensity of said gamma radiation to known gamma and neutron cross sections for the fissile and fertile nuclides contained in the sample to obtain the quantitative assay.

2. The method as described in claim 1, wherein said pulsed gamma radiation has photon energy in excess of about 10 MeV.

3. The method as described in claim 2, wherein said pulsed gamma radiation is filtered to remove photons of lower energy than about 2 MeV before impinging on the sample.

4. The method as described in claim 3, wherein said photoneutron thermalization step is caused to be substantially completed within about 0.5 ms after said termination of a particular gamma radiation pulse.

5. The method as described in claim 4, wherein said prompt fast neutron measurement step is performed between about 0.5 and 2.5 ms after said termination of a particular gamma radiation pulse in order to determine the number of thermal-neutron-induced fissions which are measurable during this time period, and wherein said delayed fast neutron measurement step is performed between about 5.5 ms after said termination of a particular gamma radiation pulse and said commencement of the following gamma radiation pulse in order to determine the number of photofissions from both fertile and fissile nuclides present in the sample which process is measurable during this later time period.

6. The method as described in claim 5, wherein said gamma radiation generated neutron flux is adjusted such that said emitted delayed fast neutron flux is comprised principally of neutrons from said photofission of fertile nuclides while allowing sufficient prompt fast neutron emission from said thermal neutron fission process in the fissile nuclides to enable said statistically significant neutron measurements to be obtained in a practical accumulation time period.

7. The method as described in claim 6, wherein said pulsed gamma radiation is derived from an electron accelerator having a beam current greater than approximately 1 ma, a pulse duration less than about 4 μs, and a pulse repetition rate within the range of substantially 1–60 Hz, the electrons generated therefrom producing said gamma radiation by a bremsstrahlung process upon striking a heavy metal target.

8. An apparatus for quantitatively evaluating total fissile and total fertile nuclide content in samples, which comprises in combination:
a. means for generating repetitively pulsed gamma radiation;
b. means for filtering said gamma radiation to remove photons of energy lower than about 2 MeV;
c. means for generating photoneutrons from a portion of said filtered gamma radiation, the remainder of said filtered gamma radiation impinging on a sample;
d. means for thermalizing said photoneutrons, whereby said photoneutrons impinge upon the sample;
e. means for measuring said thermalized photoneutron flux in the vicinity of the sample during time intervals in between the termination of a particular gamma radiation pulse and the commencement of the following one;
f. means for measuring the intensity of said gamma radiation in the vicinity of the sample;
g. means for measuring prompt and delayed fast neutron emission from the sample resulting from the photofission of fertile and fissile nuclides interacting with a substantial portion of said remainder of said filtered gamma radiation, and from fission of fissile nuclides capturing said thermalized photoneutrons during said time intervals; and
h. means for accumulating a plurality of said prompt and delayed fast neutron emission measurements, and a plurality of said thermalized neutron flux measurements until statistically significant measurements are obtained, whereby said accumulated emitted prompt and delayed fast neutron measurements normalized by said accumulated thermalized neutron flux measurements and said intensity of said gamma radiation can be related to known gamma radiation and neutron cross sections for the fissile and fertile nuclides contained in the sample to obtain the quantitative assay.

9. The apparatus as described in claim 8, wherein said photoneutron thermalization means includes the walls of a chamber, said chamber surrounding the sample.

10. The apparatus as described in claim 9, wherein said thermalized photoneutron flux measuring means includes at least one bare low pressure $^3$He proportional counter located inside said chamber in the vicinity of the sample.

11. The apparatus as described in claim 10, wherein said prompt and delayed fast neutron emission measurement means includes at least one high pressure $^3$He proportional counter surrounded by polyethylene which is in turn surrounded by cadmium foil, in order to block said thermalized photoneutrons, and located within said chamber in the vicinity of the sample.

12. The apparatus as described in claim 11, wherein said pulsed gamma radiation means further comprises:
a. an electron accelerator capable of providing greater than about 1 ma of electron beam current in short duration pulses at a repetition rate between 1 and 60 Hz, and at energies in excess of about 10 MeV; and
b. a target attached to the output of said linear accelerator which generates bremsstrahlung radiation when bombarded with said short pulses of electrons, said bremsstrahlung radiation thereby containing photons with energy in excess of about 10 MeV.

13. The apparatus as described in claim 12, wherein said filtering means includes a polyethylene slab placed between said target and said chamber.

14. The apparatus as described in claim 13, wherein said chamber wall includes a thick polyethylene inner wall surrounded by a layer of cadmium foil which is further surrounded by a thick outer wall of borated polyethylene, said cadmium and borated polyethylene layers being intended to reduce the effects of stray neutrons generated by said electron accelerator away from the direction of said electron beam.

15. The apparatus as described in claim 14, wherein said target includes niobium foil.

16. The apparatus as described in claim 15, wherein said neutron generating means includes a beryllium sheet.

17. The apparatus as described in claim 16, wherein each of said bare low pressure $^3$He proportional counters further comprises an about 2.5 cm diameter metal tube, approximately 51 cm long containing about 1% $^3$He and 99% $^4$He at low pressure.

18. The apparatus as described in claim 17, wherein each of said high pressure $^3$He proportional counters further comprises an about 5 cm diameter metal tube, approximately 34 cm long containing about 3 atmospheres of $^3$He and surrounded by about 1.25 cm of polyethylene which is in turn surrounded by about 1.7 mm thick cadmium foil.

19. The apparatus as described in claim 18, wherein said polyethylene inner chamber wall is about 10 cm thick, said surrounding cadmium foil is approximately 0.6 mm thick, and said borated polyethylene outer chamber wall is about 10 cm thick.

* * * * *